United States Patent
Lee et al.

(10) Patent No.: US 9,671,382 B2
(45) Date of Patent: Jun. 6, 2017

(54) METHYLBENZENE GAS SENSOR USING CHROME-DOPED NICKEL OXIDE NANOSTRUCTURES AND METHOD FOR PRODUCING SAME

(71) Applicant: KOREA UNIVERSITY RESEARCH AND BUSINESS FOUNDATION, Seoul (KR)

(72) Inventors: Jong-Heun Lee, Seoul (KR); Hyo-Joong Kim, Seoul (KR); Jee-Uk Yoon, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/646,939

(22) PCT Filed: Mar. 11, 2014

(86) PCT No.: PCT/KR2014/002011
§ 371 (c)(1),
(2) Date: May 22, 2015

(87) PCT Pub. No.: WO2014/171634
PCT Pub. Date: Oct. 23, 2014

(65) Prior Publication Data
US 2016/0025695 A1     Jan. 28, 2016

(30) Foreign Application Priority Data
Apr. 18, 2013 (KR) .......... 10-2013-0042633

(51) Int. Cl.
*G01N 33/00* (2006.01)
*G01N 27/12* (2006.01)

(52) U.S. Cl.
CPC ....... *G01N 33/0036* (2013.01); *G01N 27/127* (2013.01)

(58) Field of Classification Search
CPC .................. G01N 27/127; G01N 33/0036
(Continued)

(56) References Cited

U.S. PATENT DOCUMENTS

2006/0235087 A1* 10/2006 Alexandridis ........ B22F 1/0018
516/78
2010/0089772 A1* 4/2010 Deshusses ........... G01N 27/127
205/781
(Continued)

FOREIGN PATENT DOCUMENTS

KR     10-2012-0067082 A     6/2012

OTHER PUBLICATIONS

Non-Patent Literature "Hydrothermal Synthesis of Metal Oxide Nanoparticles in Supercritical Water", H. Hayashi and Y. Hakuta, published Jun. 25, 2010.*

(Continued)

*Primary Examiner* — Laura Martin
*Assistant Examiner* — Irving A Campbell
(74) *Attorney, Agent, or Firm* — Oblon, McClelland, Maier & Neustadt, L.L.P.

(57) ABSTRACT

Provided is a gas sensor comprising a gas-sensitive layer consisting of nickel oxide (NiO) doped with chrome (Cr) so as to selectively detect methylbenzene gas. The gas sensor, according to the present invention, has a gas-sensitive layer consisting of Cr-doped NiO. The gas sensor exhibits superior selectivity for methylbenzene gas when compared to other gases. The gas sensor can be easily and mass produced according to the production method of the present invention and is not affected by the microstructures of the material forming the gas-sensitive layer. The present invention (Continued)

relates to a gas sensor exhibits a negligible sensitivity of benzene, formaldehyde, and alcohol and exhibits significantly high selectivity and sensitivity of methylbenzene gas such as xylene and toluene when the NiO sensor material with a hierarchical structure favorable to gas dispersion and response is doped with Cr.

8 Claims, 7 Drawing Sheets

(58) Field of Classification Search
 USPC .......................................................... 73/31.05
 See application file for complete search history.

(56) References Cited

U.S. PATENT DOCUMENTS

| 2010/0147684 | A1* | 6/2010 | Park | G01N 27/127 204/431 |
|---|---|---|---|---|
| 2012/0156099 | A1* | 6/2012 | Zhong | B82Y 15/00 422/82.02 |
| 2012/0212242 | A1* | 8/2012 | Masel | G01N 27/127 324/693 |

OTHER PUBLICATIONS

Non-Patent Literature "L-Lysine assisted synthesis of beta-Ni(OH)2 hierarchical hollow microspheres and their enhanced electrochemical capacitance performance", Yan et al., published Sep. 12, 2012.*

International Search Report issued Jul. 11, 2014 in PCT/KR2014/002011 (with English language translation).
Perumal Elumalai, et al., "$NO_2$ sensing properties of YSZ-based sensor using NiO and Cr-doped NiO sensing electrodes at high temperature" Ionics, vol. 15, No. 4, May 26, 2009, pp. 405-411.
Ana M. Ruiz, et al., "Cr-doped $TiO_2$ gas sensor for exhaust $NO_2$ monitoring" Sensors and Actuators B Chemical, vol. 93, No. 1, 2003, pp. 509-518.
Yongxiang Li, et al., "Gas sensing properties of p-type semiconducting Cr-doped $TiO_2$ thin films" Sensors and Actuators B Chemical, vol. 83, No. 1, 2002, pp. 160-163.
Hyo-Joong Kim, et al., "Ultraselective and sensitive detection of xylene and toluene for monitoring indoor air pollution using Cr-doped NiO hierarchical nanostructures" Nanoscale, vol. 5, No. 15, May 23, 2013, pp. 7066-7073.
Qureshi A et al., "Preparation and characterization of Li and Ti codoped NiO nanocomposites for gas sensors applications", Sensors and Actuators B: Chemical, 2009, 135 (2), pp. 537-540.
Bin Liu et al., "Synthesis and enhanced gas-sensing properties of ultralong NiO nanowires assembled with NiO nanocrystals", Sensors and Actuators B: Chemical, 2011, 156 (1), pp. 251-262.
Predanocy M et al., "Sputtered NiO thin films for organic vapours testing", Advanced Semiconductor Devices&Microsystems (ASDAM), 2012 Ninth International Conference on, IEEE, Nov. 11, 2012, pp. 291-294.
Isabel Sayago et al., "Detection of Toxic Gases by a Tin Oxide Multisensor", IEEE Sensors Journal, Oct. 2002, 2 (5), pp. 387-393.
Kang-Min Kim et al., "Selective Detection of NO2 Using Cr-Doped CuO Nanorods", Sensors, Jun. 11, 2012, 12 (12), pp. 8013-8025.

* cited by examiner

Comparative Example 1

Example 1-1

Example 1-2

Example 1-3

METHYLBENZENE GAS SENSOR USING CHROME-DOPED NICKEL OXIDE NANOSTRUCTURES AND METHOD FOR PRODUCING SAME

TECHNICAL FIELD

The present invention relates to an oxide semiconductor gas sensor and a method for fabricating the same. More specifically, the present invention relates to a gas sensor having a new composition specialized for the detection of specific target gases and a method for fabricating the gas sensor.

BACKGROUND ART

Oxide semiconductor gas sensors can be miniaturized and integrated to desired sizes, are inexpensive, have high sensitivity and fast response, and can detect gas concentrations as electric signals using simple circuits. Due to these advantages, oxide semiconductor gas sensors are widely used in various applications, including detection of explosive gases, detection of exhaust gases from automobiles, measurement of drivers' blood alcohol levels, and detection of industrial gases. With the recent advances in high-tech industries and rapidly growing interest in human health and environmental pollution, there is a need for gas sensors for more precise detection of indoor/outdoor environmental gases, gas sensors for self-diagnosis of diseases, and gas sensors that can be used in high-performance artificial olfactory sensors mountable on mobile devices.

Some gases need to be detected. Among such gases, volatile organic compounds are known to be harmful to humans and are released from various sources, such as articles of furniture, solvents, and paints. Thus, it is very important to detect the concentrations of harmful volatile organic compounds in indoor environments. Representative substances harmful to humans in indoor/outdoor environments are volatile organic compounds, such as benzene, xylene, toluene, formaldehyde, and alcohol. Particularly, benzene, xylene, and toluene are aromatic hydrocarbons that have similar molecular structures. However, benzene, xylene, and toluene have different influences on humans. Benzene is known as a carcinogenic substance that can cause cancers, such as leukemia, whereas xylene and toluene were reported to cause various respiratory and nervous system diseases, such as ophthalmopathy and migraine.

Most oxide semiconductor gas sensors show comparable or similar sensitivities to the above five volatile organic compounds. However, the volatile organic compounds should be individually selectively sensed because they have different influences on humans as stated above. In the case where a sensor fails to separately sense the aromatic hydrocarbons and simply senses the total amount of the aromatic hydrocarbons, the problem arises in that it is impossible to appropriately decide how to respond to and solve individual sources of pollution. Alcohol gas occurs frequently and formaldehyde is also produced at a significantly high concentration during indoor activities such as cooking and drinking. For these reasons, gas sensors for detecting indoor aromatic environmental pollutants are required to have low cross-sensitivities to alcohol and formaldehyde. However, most oxide semiconductor gas sensors developed hitherto are highly sensitive to alcohol.

DISCLOSURE

Technical Problem

One object of the present invention is to provide an oxide semiconductor gas sensor with improved performance that senses selectively and sensitively volatile organic compounds, particularly methylbenzene gases, including xylene and toluene that have similar influences on humans.

A further object of the present invention is to provide a method for fabricating the oxide semiconductor gas sensor.

Technical Solution

One aspect of the present invention provides a gas sensor for the detection of methylbenzene gases including a gas sensing layer composed of nickel oxide (NiO) doped with chromium (Cr).

A further aspect of the present invention provides a method for fabricating the gas sensor, including forming chromium-doped nickel oxide nanostructures and forming a gas sensing layer using the nanostructures.

Advantageous Effects

The gas sensor of the present invention is fabricated using nickel oxide doped with chromium. This chromium doping enables control over the concentration of holes, achieving ultrahigh sensitivity of the gas sensor. In addition, the surface of nickel oxide is functionalized by the catalysis of chromium, which allows the gas sensor to selectively detect methylbenzene gases as harmful environmental gases, such as xylene and toluene that have similar influences on humans.

The gas sensor of the present invention uses surface-modified nanostructures, such as chromium-doped nickel oxide nanostructures. The addition of chromium increases the reaction of nickel oxide with methylbenzene gases as specific target gases. Particularly, the gas sensor of the present invention has very low cross-sensitivity to benzene gas, enabling selective detection of methylbenzene gases as harmful environmental gases. Therefore, the gas sensor of the present invention can advantageously provide an appropriate solution to harmful environmental gases.

In addition, the gas sensor of the present invention does not detect alcohol gas occurring during indoor activities, such as cooking and drinking, due to its low alcohol sensitivity and is thus advantageous in selectively sensing xylene and toluene. Furthermore, the gas sensor of the present invention is very advantageous in selectively sensing xylene and toluene because it has very low sensitivity to formaldehyde, which is usually detected at a high concentration indoors.

Chromium-doped nickel oxide nanostructures used as raw materials in the gas sensor of the present invention can be easily synthesized at one time on a large scale. According to the method of the present invention, the same sensing properties of the gas sensor can be obtained irrespective of how to add the chromium and the structure of the nickel oxide. The methylbenzene gas sensor can provide bring better results in terms of selectivity over traditional gas sensors.

According to the present invention, the use of chromium-doped nickel oxide nanostructures allows the p-type oxide semiconductor gas sensor to have greatly increased sensitivity and superior stability against external humidity.

BEST MODE

The present invention provides a gas sensor for the detection of methylbenzene gases including a gas sensing layer composed of nickel oxide doped with chromium. The doped nickel oxide may have a hierarchical structure in which plate-like primary particles aggregate to form spherical particles. The chromium may be added in an amount of 0.2 to 2 at %.

The present invention also provides a method for fabricating the gas sensor. The method includes forming chromium-doped nickel oxide nanostructures and forming a gas sensing layer using the nanostructures. The step of forming chromium-doped nickel oxide nanostructures may include: mixing a nickel precursor with a chromium precursor in a mixed solvent of anhydrous ethanol and deionized water to prepare a raw material solution; subjecting the raw material solution to hydrothermal synthesis by heating; and washing the reaction solution by centrifugation and drying the precipitate. Lysine may be further added to the raw material solution.

[Mode for Invention]

Hereinafter, preferred embodiments of the present invention will be described in detail with reference to the accompanying drawings. The embodiments of the present invention, however, may be changed into several other forms, and the scope of the present invention should not be construed as being limited to the following embodiments. The embodiments of the present invention are intended to more comprehensively explain the present invention to those skilled in the art. Accordingly, the shapes of elements or the like shown in figures are exaggerated to emphasize distinct explanation.

The gas sensor of the present invention includes a gas sensing layer composed of nickel oxide doped with chromium. Prior to the present invention, high selectivity of chromium-doped nickel oxide only for methylbenzene gases has never been known in the art. To the best of our knowledge, this is the first report on the use and effect of chromium-doped nickel oxide.

Figure 1:
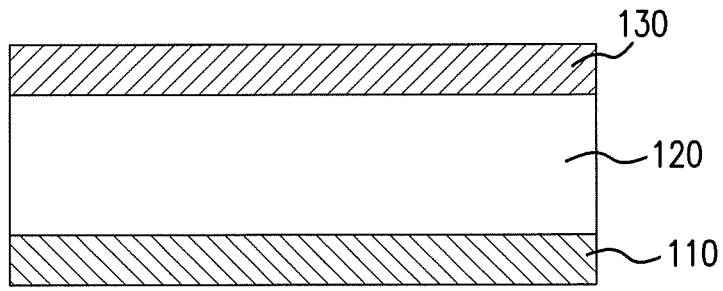
FIG. 1 and FIG. 2 are schematic cross-sectional views illustrating exemplary structures of a gas sensor according to the present invention.
Figure 2:
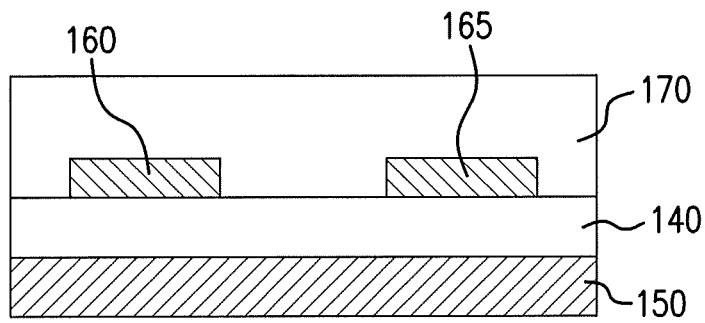

FIGS. 1 and 2 are schematic cross-sectional views illustrating exemplary structures of the gas sensor according to the present invention. However, the gas sensor of the present invention is not limited to the structures illustrated in the figures and may have any structure that includes a gas sensing layer composed of nickel oxide doped with chromium.

In the gas sensor structure illustrated in FIG. 1, electrodes 130 and 110 are formed on the upper and lower surfaces of a gas sensing layer 120, respectively. In the gas sensor structure illustrated in FIG. 2, a microheater 150 is disposed under a substrate 140, two electrodes 160 and 165 are formed on the substrate 140, and a gas sensing layer 170 is formed thereon. The gas sensing layers 120 and 170 are composed of chromium-doped nickel oxide. If needed, the amount of chromium in each gas sensing layer may be varied.

In the present invention, taking advantage of a high degree of solid solution of nickel oxide for chromium, chromium is substituted into the lattice of nickel oxide so that the concentration of holes can be controlled. This substitution improves the gas sensing properties of the gas sensor through the electronic sensitization effect. Simultaneously with this, the inherent oxidative catalytic activity of chromium enables the gas sensor to selectively sense methyl group-containing hydrocarbon gases, that is to say, methylbenzene gases, for example, xylene and toluene. The amount of chromium added is preferably from 0.1 to 2 at % with respect to the amount of nickel oxide, as confirmed by the results of experiments conducted in the Examples section that follow. If the chromium is added in an amount of less than 0.2 at % or exceeding 2 at %, the sensitivity of the gas sensor to methylbenzene gases may deteriorate. Specifically, if the chromium is added in an amount of less than 0.2 at %, a variation in the resistance of the sensor is small, resulting in a small change in the sensitivity of the sensor due to the electronic sensitization mechanism. Meanwhile, if the chromium is added in an amount exceeding 2 at %, a secondary phase is formed, and as a result, a sufficient increase in sensitivity is not obtained.

The gas sensor including the gas sensing layer 120 or 170 composed of chromium-doped nickel oxide is considered a p-type oxide semiconductor gas sensor. When negatively charged oxygen is adsorbed to the surface of the p-type oxide semiconductor, holes around the surface gather to form a hole accumulation layer. When the p-type oxide semiconductor is exposed to a reducing gas, the reducing gas reacts with the negatively charged oxygen to inject electrons into the hole accumulation layer. As a result of combination of the electrons and holes, the concentration of holes decreases and the thickness of the hole accumulation layer is reduced, resulting in an increase in the resistance of the sensor. Meanwhile, when the p-type oxide semiconductor is exposed to an oxidizing gas, the thickness of the hole accumulation layer increases, resulting in a reduction in the resistance of the sensor. Based on the gas sensing mechanism that a change in conductivity is caused by the surface adsorption of gas, the gas sensor of the present invention is operated.

Gas sensors using n-type oxide semiconductors ($SnO_2$, $In_2O_3$, $Cr_2O_3$, and ZnO) reported to date simultaneously show high sensitivities to a variety of gases, indicating their poor gas selectivity. The gas sensors sensitively respond to humidity in air due to their air resistance as high as several to several tens of MΩ. When the gas sensors react with humidity, the air resistance of the gas sensors varies drastically, deteriorating the stability of the gas sensors. In contrast, gas sensors using p-type oxide semiconductors having an air resistance as low as a few to a few tens of KO undergo minimal change in resistance in air during long-term operation, indicating their long-term stability. However, p-type oxide semiconductors suffer from difficulty in detecting gases at low concentrations because they have relatively low gas sensitivity compared to n-type oxide semiconductors. The gas sensor of the present invention can be used to develop gas sensor devices with high sensitivity and reliability because it uses a p-type oxide semiconductor that undergoes minimal change in resistance and is highly sensitive.

In the present invention, chromium is doped into nickel oxide as a sensing material whose structure may be varied. This chromium doping allows the gas sensor to have higher stability than n-type oxide semiconductor gas sensors and increases the sensitivity of the gas sensor to methylbenzene gases by several times compared to that of conventional gas sensors irrespective of the structure of the nickel oxide. High selectivity of the gas sensor for methylbenzene gases can be obtained. According to the present invention, chromium is substituted into the lattice of nickel oxide as a p-type oxide semiconductor whose structure may be varied. This substitution can bring about a remarkable improvement in the sensitivity of the nickel oxide semiconductor gas sensor to methylbenzene gases, while at the same time attaining high selectivity of the gas sensor for methylbenzene gases. The p-type oxide semiconductor gas sensor has the advantages of superior long-term stability and high selectivity as well as high sensitivity. These advantages are expected to contribute to the commercialization of the p-type oxide semiconductor gas sensor.

As can be seen from the Examples section that follows, the chromium-doped nickel oxide constituting the gas sensing layers 120 and 130 may be in the form of a nanopowder that has a hierarchical structure produced by a one-step process through hydrothermal synthesis. The hierarchical structure refers to a structure in which plate-like primary particles aggregate to form spherical particles. The hierarchical structure has a large surface area, which is advantageous for gas diffusion.

However, improved selective sensitivity to methylbenzene gases by the addition of chromium is found in all structures of nickel oxide as a sensing material without being limited to a particular structure of nickel oxide. This makes the present invention more meaningful. The gas sensor of the present invention may have various compositions and structures, for example, by doping chromium into commercial nickel oxide powders. As the powder size and pore size decreases to the nanometer range, the powder is advantageous in gas diffusion. Accordingly, it is preferred that the chromium-doped nickel oxide used as a gas sensing material in the present invention is in the form of nanostructures. According to the method of the present invention, the gas sensor is fabricated using chromium-doped nickel oxide nanostructures, such as a nanopowder having a hierarchical structure, which will be described below.

Figure 3:
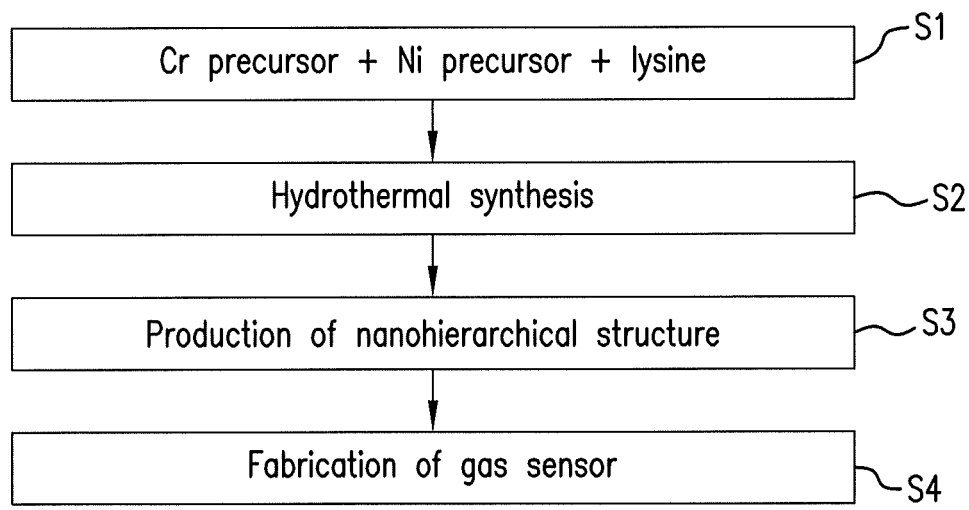
FIG. 3 is a flowchart illustrating a method for fabricating a gas sensor according to an embodiment of the present invention.
Figure 4A:
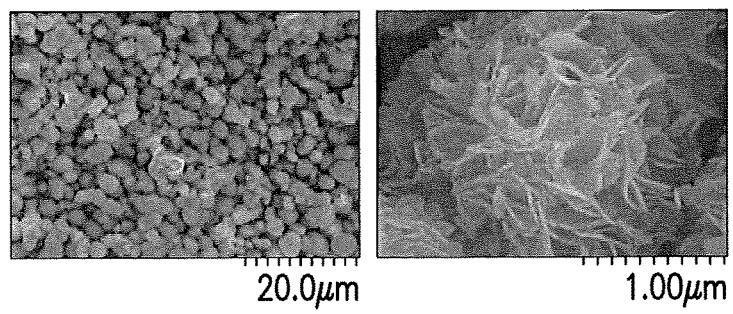
FIG. 4A, FIG. 4B, FIG. 4C and FIG. 4D show SEM images of nanostructures produced in Comparative Example 1 and Examples 1-1, 1-2, and 1-3, respectively.
Figure 4B:
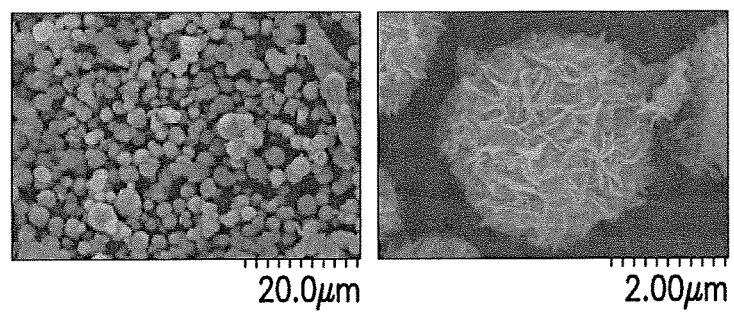
Figure 4C:
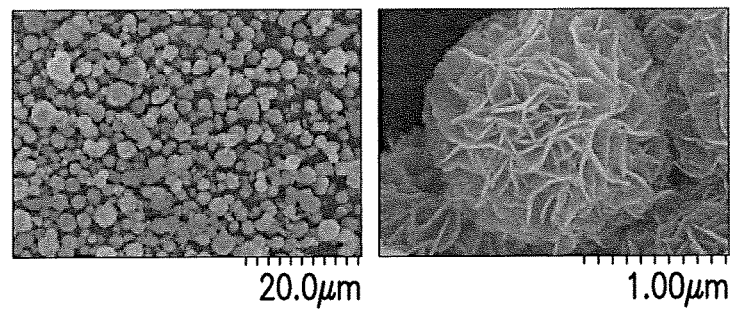
Figure 4D:
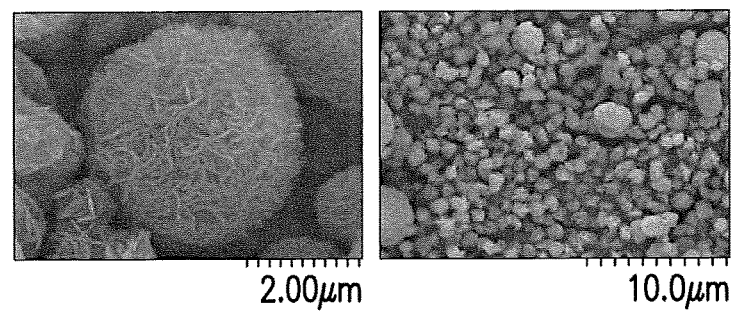

FIG. 3 is a flowchart illustrating a method for fabricating a gas sensor according to an embodiment of the present invention.

First, a nickel precursor and lysine are added to a mixed solvent of anhydrous ethanol and deionized water. The solution is stirred. To the solution is further added a chromium precursor, followed by stirring to prepare a raw material solution (step S1). The reason for the lysine addition is because self-assembly between the positively charged amine groups and the negatively charged carboxyl group of the lysine leads to the formation of well-aligned and periodically porous nanostructures that facilitate gas diffusion and have a large specific surface area, thus being advantageous in sensing gases.

Next, the raw material solution is subjected to hydrothermal synthesis by heating (step S2). For example, the heating is performed at 180° C. for 4 hours.

The reaction solution is washed by centrifugation and dried to prepare a nanopowder having a hierarchical structure (step S3). If needed, the powder is annealed, for example, at 500 to 600° C. for 1 to 2 hours. This annealing is not necessarily performed but would be desirable because it is effective in removing residual organic materials and imparting strength to the powder.

Next, a gas sensing layer is formed using the chromium-doped nickel oxide powder, completing the fabrication of the gas sensor illustrated in FIG. 1 or 2 (step S4). The gas sensor can be fabricated by the following procedure.

First, the chromium-doped nickel oxide powder obtained in step S3 is dispersed in an appropriate solvent or binder. The dispersion is applied to a proper substrate, for example, the substrate 140 illustrated in FIG. 2 (under which the microheater 150 is disposed and on which the two electrodes 160 and 165 are formed). Herein, the term "application" is intended to include various techniques, such as printing, brushing, blade coating, dispensing, and micropipette dropping. Next, the solvent is removed to form a gas sensing layer. If needed, heating, i.e. annealing, may be performed to assist in removing the solvent.

Alternatively, the gas sensor may be fabricated by the following procedure. A chromium precursor solution for chromium doping is applied to a commercial nickel oxide powder or nanopowder, followed by appropriate annealing. The resulting chromium-doped nickel oxide powder is used to fabrication the gas sensor.

Example 1

0.010 mol of nickel (II) acetate tetrahydrate ($Ni(C_2H_3OO)_2 \cdot 4H_2O$, 99.998% trace metals basis, Sigma-Aldrich Co.) and 0.010 mol of L(+)-lysine ($C_6H_{14}N_2O_2$, 98%, Sigma-Aldrich Co.) were added to a mixed solvent of 45 ml of anhydrous ethanol and 5 ml of deionized water. The solution was stirred for 5 min. To the solution was added chromium (III) acetylacetonate ($Cr(C_5H_7O_3)_3$, 99.99% trace metals basis, Sigma-Aldrich Co.). The amount of the chromium precursor added was determined such that the ratio of Cr/Ni was 0.5 at % (Example 1-1), 1 at % (Example 1-2) or 2 at % (Example 1-3). After stirring for 10 min, the solution was subjected to hydrothermal synthesis at 180° C. for 4 h. After completion of the reaction, the reaction solution was washed five times by centrifugation and dried for 24 h to yield a precursor in the form of a fine powder having a nanohierarchical structure. The precursor was annealed at 600° C. for 2 h to obtain chromium-doped nickel oxide having a nanohierarchical structure. The chromium-doped nickel oxide was mixed with an organic binder, screen printed on an alumina substrate on which an Au electrode had been formed, dried at 100° C. for 5 h, and annealed at 500° C. for 1 h, completing the fabrication of the gas sensor illustrated in FIG. 1. The sensor was placed in a quartz tube high temperature electric furnace (inner diameter 30 m) at 400° C., and pure air and air+mixed gas were alternately fed into the furnace. During the feeding, changes in the resistance of the sensor were measured. The gases were previously mixed and their concentrations were rapidly varied using a 4-way valve. The total flow rate was fixed at 500 sccm so that there was no temperature difference when the gas concentrations were varied.

Example 2

1 g of a commercial powder of nickel oxide (NiO, trace metals basis, Sigma-Aldrich Co.) was added to an aqueous solution in which Cr was present in an amount of 1 at %, based on the amount of Ni. The mixture was stirred at 100° C. until the solvent was completely volatilized, followed by annealing at 600° C. for 2 h to obtain chromium-doped nickel oxide nanoparticles. Thereafter, a sensor was fabricated using the chromium-doped nickel oxide nanoparticles and the gas sensing properties of the sensor were measured in the same manner as in Example 1.

Comparative Example 1

A gas sensor was fabricated and the gas sensing properties of the sensor were measured in the same manner as in Example 1, except that the use of chromium (III) acetylacetonate was omitted to obtain a pure nickel oxide nanopowder having a hierarchical structure.

Comparative Example 2

A sensor was fabricated and the gas sensing properties of the sensor were measured in the same manner as in Example 1, except that rhodium (III) chloride hydrate ($RhCl_3.3H_2O$, ≥99.9% trace metals basis, Sigma-Aldrich Co.) was added instead of chromium (III) acetylacetonate to produce a rhodium (Rh)-doped nickel oxide nanopowder having a hierarchical structure. The amount of the rhodium precursor added was determined such that the ratio of Rh/Ni was 0.5 at %.

Comparative Example 3

A sensor was fabricated and the gas sensing properties of the sensor were measured in the same manner as in Example 1, except that antimony (Sb, 99.5% trace metals basis, Sigma-Aldrich Co.) was added instead of chromium (III) acetylacetonate to produce an antimony (Sb)-doped nickel oxide nanopowder having a hierarchical structure. The amount of the antimony added was determined such that the ratio of Sb/Ni was 0.5 at %.

Comparative Example 4

The characteristics of the sensors were measured at different temperatures. As a result, the sensors exhibited p-type semiconductor characteristics because their resistances were increased in all reducing gases. The gas response of each sensor was defined as $R_g/R_a$ ($R_g$: resistance of the device in the corresponding gas, $R_a$: resistance of the device in air). The selectivity of the sensor for a target gas was determined from differences in the sensitivities of the sensor to the target gas and the other gases.

When the resistance of each sensor in air was kept constant, the atmosphere was suddenly changed to xylene, toluene, benzene, formaldehyde or ethanol (5 ppm) as a target gas. Thereafter, when the resistance of the sensor in the target gas was kept constant, the atmosphere was suddenly changed to air. At this time, a change in the resistance of the sensor was measured. When the final resistance reached upon exposure to the gas was $R_g$ and the resistance in air was $R_a$, the time at which 90% of the resistance difference ($R_g$-$R_a$) is changed to reach a point close to the resistance $R_g$ was defined as 90% response time. The resistance $R_g$ decreased when the atmosphere was changed to air after exposure to the gas. The time at which 90% of the resistance difference ($R_g$-$R_a$) is changed to reach a point close to the resistance $R_a$ was defined as 90% recovery time.

FIG. 4A, FIG. 4B, FIG. 4C and FIG. 4D show SEM images of the nanostructures produced in (a) Comparative Example 1 (pure nickel oxide), (b) Example 1-1 (0.5 at % chromium-doped nickel oxide), (c) Example 1-2 (1 at % chromium-doped nickel oxide), and (d) Example 1-3 (2 at % chromium-doped nickel oxide), respectively. Each nanostructure was found to have a hierarchical structure in which plate-like primary particles aggregated to form spherical particles. The addition of a small amount of the polar deionized water was responsible for the growth of primary particles into plate-like particles. The nanostructures of Example 1-1 and Comparative Example 1 had the same structure and size irrespective of the chromium addition and were also observed to have the same specific surface area. As the amount of chromium increased, the specific surface area increased and the average particle size decreased (Examples 1-2 and 1-3). The inventive gas sensors were structurally optimized through the hierarchical nanostructures that were advantageous for gas diffusion and had a large specific surface area.

Figure 5:
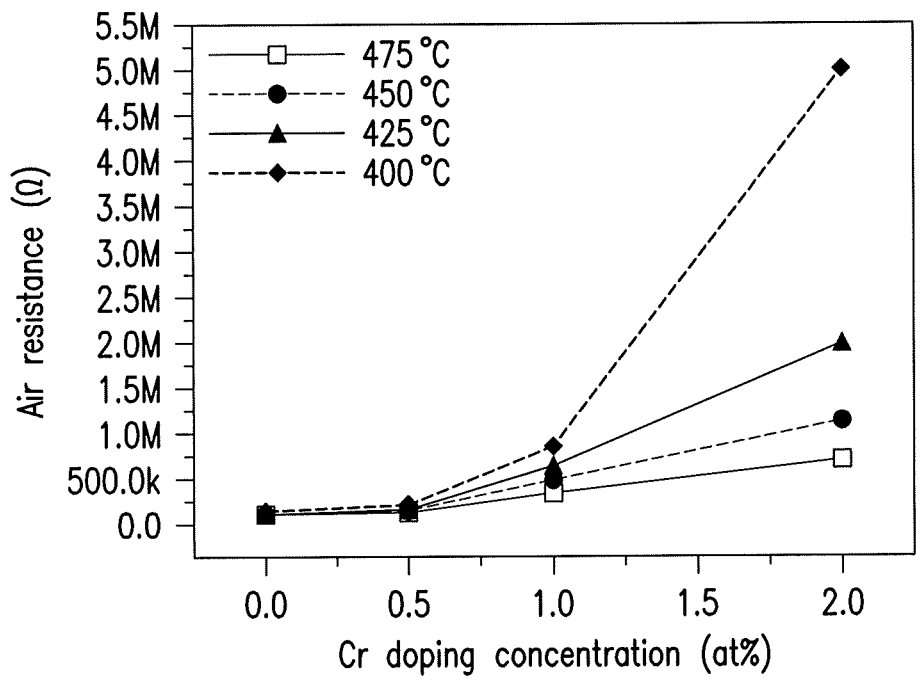
FIG. 5 shows the air resistances of gas sensors fabricated in Examples 1-1, 1-2, and 1-3 and Comparative Example 1.

FIG. 5 shows the air resistances of the gas sensors fabricated in Examples 1-1, 1-2, and 1-3 and Comparative Example 1. In FIG. 5, the x-axis shows the doping concentration of chromium and the y-axis shows the air resistance. The air resistances of the gas sensors were measured at four varying sensing temperatures by 25° C. from 400° C. to 475° C. Referring to FIG. 5, the air resistances of the gas sensors increased with increasing amount of chromium added. These results demonstrate the substitution of chromium into the lattice of nickel oxide. This substitution of $Cr^{3+}$ into the lattice of nickel oxide ($Ni^{2+}$) reduces the concentration of holes, giving rise to an increase in air resistance. This air resistance increase tended to be more pronounced with decreasing sensing temperature.

Figure 6:
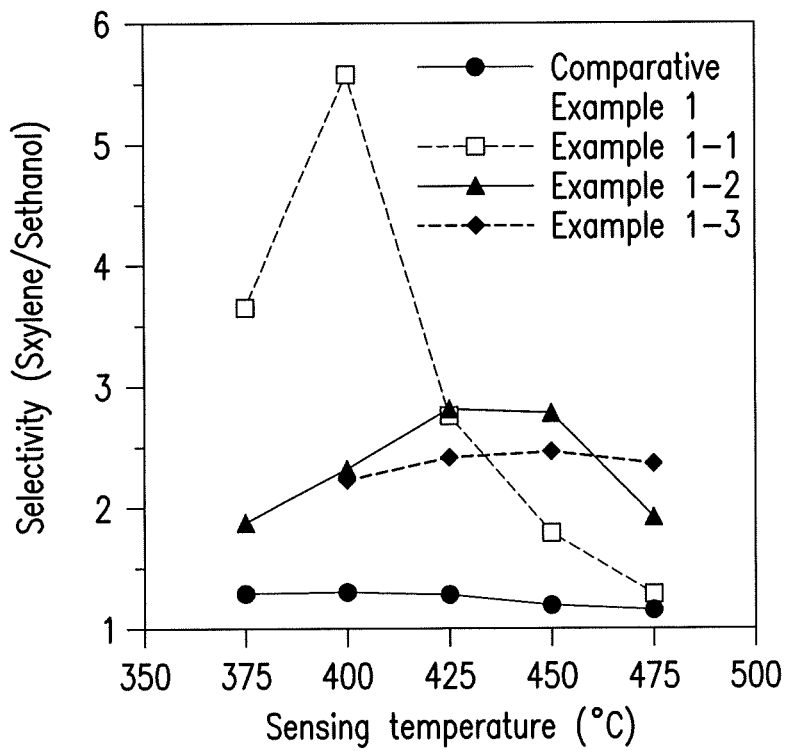
FIG. 6 is a graph showing changes in the temperature dependent selectivity of gas sensors fabricated in Examples 1-1, 1-2, and 1-3 and Comparative Example 1 for xylene gas over ethanol gas ($S_{xylene}/S_{ethanol}$).

The influences of the chromium addition on the selectivities of the gas sensors for xylene gas are shown in FIG. 6. In FIG. 6, the x-axis shows the sensing temperature and the y-axis shows the selectivity ($S_{xylene}/S_{ethanol}$). Referring to FIG. 6, the gas sensor of Comparative Example 1 showed almost similar sensitivities to xylene gas and ethanol gas (each 5 ppm), revealing that the gases are very difficult to selectively detect with the gas sensor. In contrast, the gas sensors of Examples 1-1, 1-2, and 1-3 showed greatly improved sensitivities to xylene gas compared to ethanol gas, demonstrating their high selectivities. This indicates that the added chromium functions as a very important catalyst that allows the gas sensors to selectively detect the methylbenzene. The selectivities of the gas sensors were compared depending on the chromium content. As a result, when the chromium content increased above a predetermined concentration, the effect of chromium to improve the selectivity was relatively decreased. The highest selectivity was obtained in Example 1-1. This means that the selectivity was most efficiently improved when chromium as a catalyst was present in a very small amount. The presence of an increased amount of chromium is believed to cause the formation of a secondary phase and to complete oxidize analyte gas before arriving to lower sensing part near the electrodes, giving rise to low selectivity. The best result was obtained in Example 1-1 when the sensing temperature was 400° C. The increased sensitivity resulting from chromium doping can be explained by the formation of defects (electron generation and nickel vacancy) during substitution of chromium into the nickel oxide lattice, bringing about a decrease in the concentration of effective charge carriers. A reduction in the number of effective charge carriers (i.e. holes) leads to an improvement in sensitivity through the electronic sensitization effect.

Figure 7:
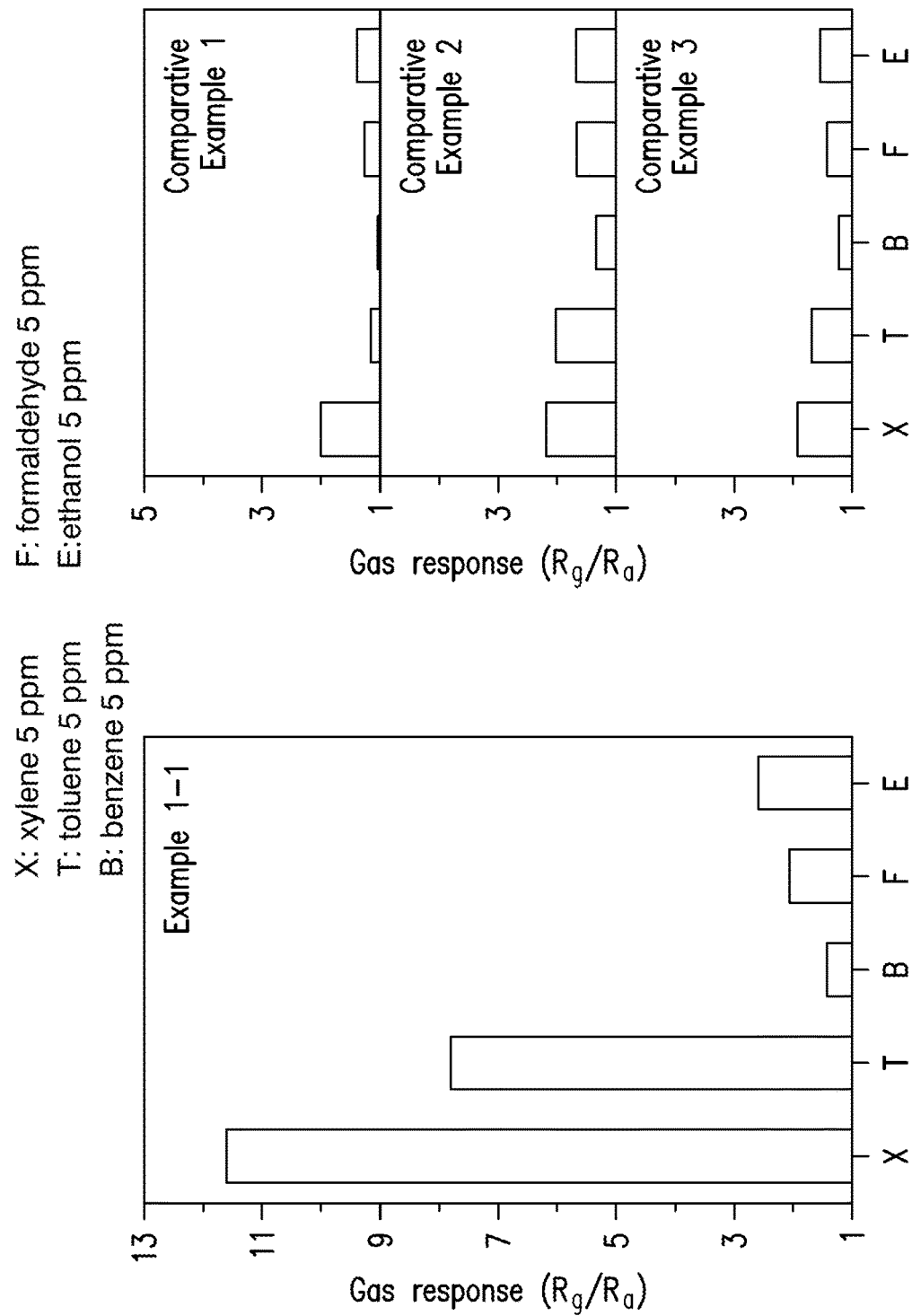
FIG. 7 graphically shows the sensitivities of gas sensors fabricated in Example 1-1 and Comparative Examples 1, 2, and 3 to various gases.

The selectivities of the gas sensors fabricated in Example 1-1 and Comparative Examples 1 (pure nickel oxide), 2 (Rh-added nickel oxide), and 3 (Sb-added nickel oxide) for various kinds of gases (X: xylene, T: toluene, B: benzene, F: formaldehyde, E: ethanol, each gas concentration: 5 ppm) were evaluated to clarify the oxidative catalytic activity of chromium. The results are shown in FIG. 7. In FIG. 7, the x-axis shows the gases and the y-axis shows the gas response defined as $R_g/R_a$.

Referring to FIG. 7, the gas sensor of Comparative Example 1 showed very low sensitivities of 1 to 1.5 to the target gases, revealing that the gases are very difficult to selectively detect with the gas sensor. The sensitivity of the Cr-added gas sensor of Example 1-1 was increased as a whole through the electronic sensitization effect resulting from a decrease in hole concentration. Particularly, the gas sensor was confirmed to have markedly increased sensitivities to methylbenzene gases (i.e. xylene and toluene). It is believed that chromium acts as a catalyst on the methyl groups of xylene and toluene gases to decompose the methylbenzene gases, achieving high sensitivity of the gas sensor. To demonstrate the specificity of chromium as a catalyst for selective detection, the gas sensing properties of the Rh- and Sb-added gas sensors of Comparative Examples 2 and 3 were measured. Both Rh and Sb functioned to reduce the concentration of holes in nickel oxide, resulting in increases in the sensitivity to the gases, but were confirmed to have no effect on selective detection of the target gases. These results lead to the conclusion that chromium is very useful as a catalyst to selectively decompose methylbenzene gases.

Figure 8A:
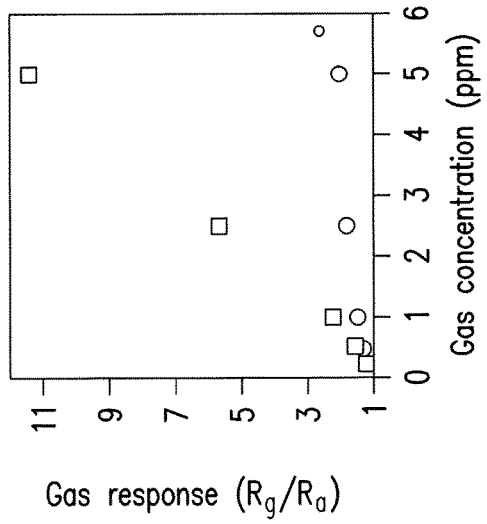
FIG. 8A, FIG. 8B, FIG. 8C and FIG. 8D show the xylene gas and ethanol gas sensing properties of gas sensors fabricated in Example 1-1 and Comparative Example 1.
Figure 8B:
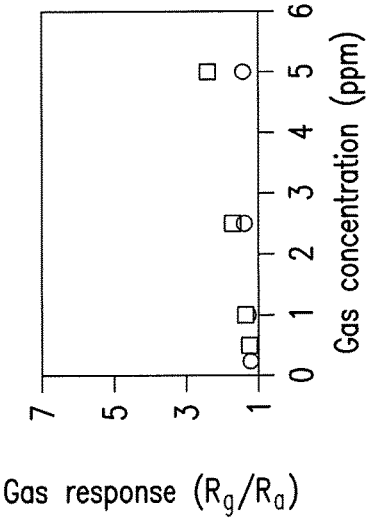
Figure 8C:
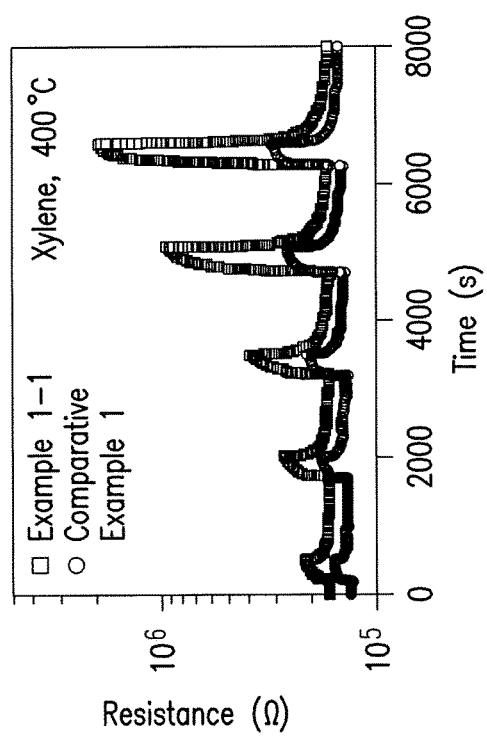
Figure 8D:
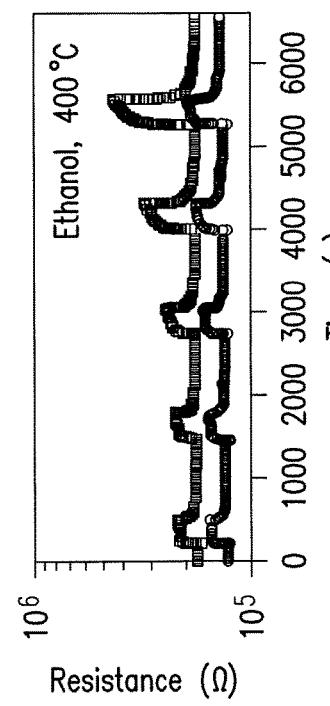

FIG. 8A, FIG. 8B, FIG. 8C and FIG. 8D show the xylene gas sensing properties of the gas sensors of (a) Example 1-1 (FIG. 8A) and (b) Comparative Example 1 (FIG. 8B) with varying gas concentrations, and the ethanol gas sensing properties of the gas sensors of (c) Example 1-1 (FIG. 8C) and (d) Comparative Example 1 (FIG. 8D) with varying gas concentrations. In FIG. 8A and FIG. 8C, the x-axis shows the time and the y-axis shows the resistance. In FIG. 8B and FIG. 8D, the x-axis shows the gas concentration and the y-axis shows the gas response.

The gas sensor of Example 1-1 showed a 1.7-fold higher sensitivity (2.42) to 5 ppm ethanol gas at an operating temperature of 400° C. than that (1.42) of the gas sensor of Comparative Example 1. In contrast, the gas sensor of Example 1-1 showed a 5.5-fold higher sensitivity (11.40) to xylene gas at an operating temperature of 400° C. than that (2.05) of the gas sensor of Comparative Example 1. These results demonstrate that the gas sensor of Example 1-1 has the ability to selectively detect even a very small amount of xylene gas (≤1 ppm) due to its increased sensitivity to xylene gas.

Figure 9A:
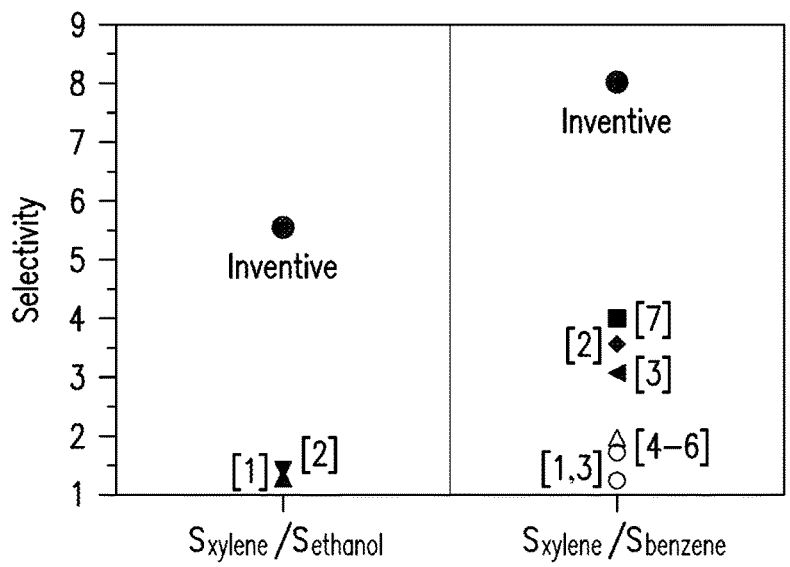
FIG. 9A and FIG. 9B the selectivities of an inventive gas sensor for xylene gas over ethanol and benzene with those of conventional gas sensors reported in the literature.
Figure 9B:
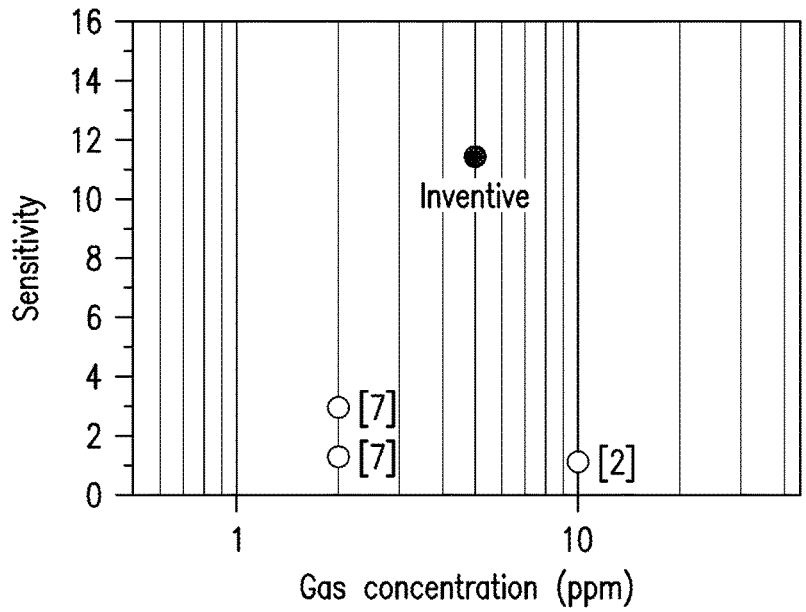

FIG. 9A and FIG. 9B compare the ability of the inventive gas sensor to selectively detect xylene gas over ethanol and benzene with that of conventional gas sensors reported in the literature. FIG. 9A is a graph showing the selectivities of the inventive gas sensor and the conventional gas sensors for xylene gas over ethanol gas ($S_{xylene}/S_{ethanol}$) and for xylene gas over benzene gas ($S_{xylene}/S_{benzene}$). Many research groups have conducted research on the use of various materials to achieve improved sensitivity to and selectivity for xylene gas. However, there has been no report on materials with 2-fold or higher selectivity for xylene over ethanol gas. It was also reported that a sensitivity of 4 or more for xylene over ethanol was difficult to attain at concentrations of 100 ppm or lower. Referring to FIG. 9A, the selectivity of the inventive gas sensor could for the methylbenzene gas was at least 5 times higher than that for ethanol gas. It can be concluded that the inventive gas sensor produced much better results than the conventional gas sensors and had the world's highest selectivity among the results of the oxide semiconductor gas sensors reported to date.

FIG. 9B shows the gas responses of the inventive gas sensors and some of the conventional gas sensors at various gas concentrations. As shown FIG. 9B, the inventive gas sensor achieved a sensitivity higher than 10 at a gas concentration lower than 5 ppm while attaining a higher selectivity than the conventional gas sensors. From these results, it can be concluded that the inventive gas sensor is suitable as a p-type oxide semiconductor gas sensor with high sensitivity and selectivity.

Figure 10:
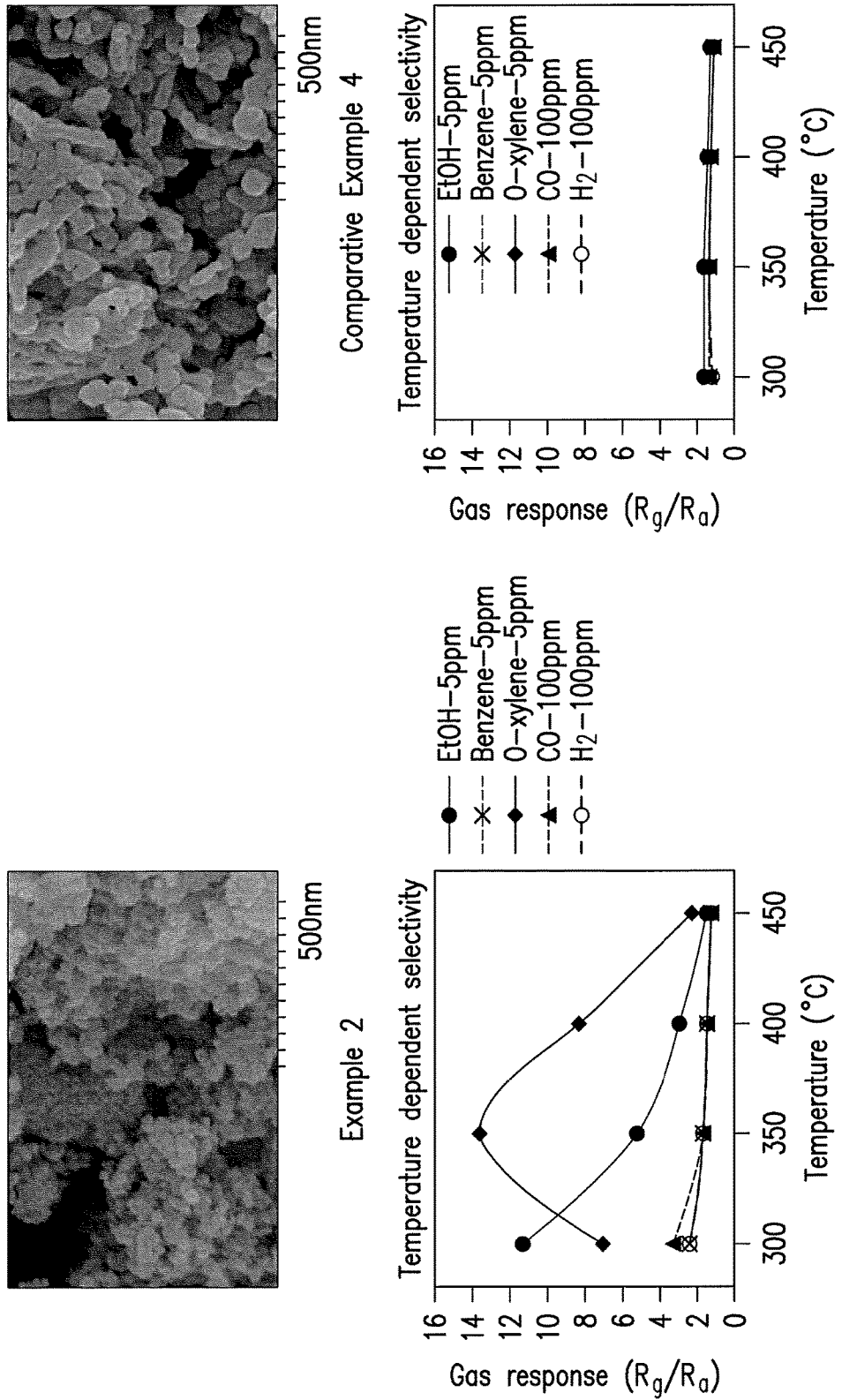
FIG. 10 shows the ethanol, xylene, benzene, CO, and $H_2$ gas sensing properties of gas sensors fabricated in Example 2 and Comparative Example 4.

In order to verify that these results are independent of the structure of nickel oxide nanoparticles, the gas sensing properties of the gas sensors of Example 2 and Comparative Example 4 were measured and are shown in FIG. 10. The commercially available nickel oxide nanoparticles showed very high responses to ethanol gas in the temperature zone of 300-450° C. and their responses to xylene gas (1.2-1.5) were substantially similar to the responses to ethanol gas. In contrast, the 1 at % Cr-added nickel oxide nanoparticles showed increased responses to both ethanol and xylene, and particularly, they showed drastically increased responses to xylene in the temperature range of 350-400° C., confirming their very high selectivity for xylene. These results reveal that Cr is effective in improving the selectivity for the methylbenzene gas irrespective of the structure of nickel oxide.

Although the present invention has been described herein with reference to the preferred embodiments thereof, it is not limited to the embodiments and it will be understood by those skilled in the art that the invention can be implemented in other specific forms without departing from the spirit and scope of the invention as defined by the appended claims. The embodiments are merely illustrative and are not to be considered as limiting the invention in all aspects. The scope of the invention is defined by the appended claims rather than by the detailed description of the invention. All changes which come within the meaning and range of equivalency of the claims are to be encompassed within the scope of the invention.

The invention claimed is:

1. A gas sensor for the detection of methylbenzene gases comprising a gas sensing layer comprising nickel oxide doped with chromium, wherein the chromium is added in an amount of 0.2 to 2 at %.

2. The gas sensor according to claim 1, wherein the chromium-doped nickel oxide has a hierarchical structure in which plate-like primary particles aggregate to form spherical particles.

3. A method for fabricating a gas sensor for the detection of methylbenzene gases, comprising forming chromium-doped nickel oxide nanostructures and forming a gas sensing layer using the chromium-doped nickel oxide nanostructures, wherein chromium is added in an amount of 0.2 to 2 at %.

4. The method according to claim 3, wherein the forming of the chromium-doped nickel oxide nanostructures comprises:
   mixing a nickel precursor with a chromium precursor in a mixed solvent of anhydrous ethanol and deionized water to prepare a raw material solution;
   subjecting the raw material solution to hydrothermal synthesis by heating to form a slurry solution comprising precipitates; and
   washing the slurry solution comprising precipitates by centrifugation and drying the precipitate,
   wherein the slurry solution is prepared by the hydrothermal reacting of raw material solution.

5. The method according to claim 4, wherein lysine is further added to the raw material solution.

6. A gas sensor for the detection of methylbenzene gases comprising a gas sensing layer comprising nickel oxide doped with chromium, wherein the chromium-doped nickel oxide has a hierarchical structure in which plate-like primary particles aggregate to form spherical particles.

7. A method for fabricating a gas sensor according to claim 6, comprising forming chromium-doped nickel oxide nanostructures and forming a gas sensing layer using the chromium-doped nickel oxide nanostructures, wherein the chromium-doped nickel oxide has a hierarchical structure in which plate-like primary particles aggregate to form spherical particles.

8. The method according to claim 7, wherein lysine is further added to the raw material solution.

* * * * *